(12) United States Patent
Kang et al.

(10) Patent No.: US 8,798,726 B2
(45) Date of Patent: Aug. 5, 2014

(54) METHOD AND APPARATUS FOR ELIMINATING MOTION ARTIFACTS OF BIO SIGNAL USING PERSONALIZED BIO SIGNAL PATTERN

(71) Applicants: Jae-min Kang, Seoul (KR); Kun-kook Park, Suwon-si (KR); Kun-soo Shin, Seongnam-si (KR)

(72) Inventors: Jae-min Kang, Seoul (KR); Kun-kook Park, Suwon-si (KR); Kun-soo Shin, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/648,054

(22) Filed: Oct. 9, 2012

(65) Prior Publication Data

US 2013/0211271 A1 Aug. 15, 2013

(30) Foreign Application Priority Data

Feb. 13, 2012 (KR) ........................ 10-2012-0014405

(51) Int. Cl.
*A61B 5/04* (2006.01)

(52) U.S. Cl.
USPC ........................................ 600/509

(58) Field of Classification Search
USPC .......................................... 600/509
See application file for complete search history.

(56) References Cited

U.S. PATENT DOCUMENTS

| 5,662,105 A | * | 9/1997 | Tien ............................ 600/336 |
| 2006/0136744 A1 | | 6/2006 | Lange |
| 2011/0098583 A1 | | 4/2011 | Pandia et al. |

FOREIGN PATENT DOCUMENTS

| JP | 11-9564 A | 1/1999 |
| JP | 2009-261723 A | 11/2009 |
| KR | 10-2003-0081903 A | 10/2003 |
| KR | 10-0750662 B1 | 8/2007 |
| KR | 10-2009-0040721 A | 4/2009 |

* cited by examiner

*Primary Examiner* — George Manuel
(74) *Attorney, Agent, or Firm* — NSIP Law

(57) ABSTRACT

An apparatus for eliminating motion artifacts in a bio signal includes a bio signal acquisition unit configured to acquire a bio signal from a patient; a reconstruction signal generator configured to generate a reconstruction signal of the acquired bio signal based on a result of comparing the acquired bio signal with a bio signal pattern of the patient generated using a bio signal measured from the patient before acquiring the bio signal from the patient; and a motion artifact elimination unit configured to eliminate motion artifacts in the acquired bio signal based on a difference between the reconstruction signal and the acquired bio signal.

19 Claims, 5 Drawing Sheets

METHOD AND APPARATUS FOR ELIMINATING MOTION ARTIFACTS OF BIO SIGNAL USING PERSONALIZED BIO SIGNAL PATTERN

CROSS-REFERENCE TO RELATED APPLICATIONS

This application claims the benefit of Korean Patent Application No. 10-2012-0014405 filed on Feb. 13, 2012, in the Korean Intellectual Property Office, the disclosure of which is incorporated herein by reference in its entirety.

BACKGROUND

1. Field

This disclosure relates to methods and apparatuses for eliminating motion artifacts in a bio signal that represents heart performance using a personalized bio signal pattern.

2. Description of Related Art

In general, a heart rate is measured based on analysis of bio signals of a person being tested. Bio signals of the heart are current or voltage signals generated by neurons or muscle cells, and the heart rate is generally measured from electrocardiogram (ECG) signals. The ECG signals are cardiac action potential waveforms. Electrical conduction occurs due to ions within a living body and electrons in a measuring system, and thus surface electrodes that are to be attached to a body of a person being tested are used. The surface electrodes measure an electric potential generated due to actions of many cells dispersed around the electrodes.

The heart rate may be measured by extracting peaks of an R-wave in the ECG waveform, measuring a period between the peaks, and calculating the heart rate within a predetermined time period from a result of the measuring. For example, the heart rate may be measured as a rate per minute (beats/min (BPM)), and typically falls within a range of about 60 to 100 beats/min (BPM) in a normal ECG.

SUMMARY

In one general aspect, a method of eliminating motion artifacts in a bio signal includes acquiring a bio signal from a patient; generating a reconstruction signal of the acquired bio signal based on a result of comparing the acquired bio signal with a bio signal pattern of the patient generated using a bio signal measured from the patient before acquiring the bio signal from the patient; and eliminating motion artifacts in the acquired bio signal based on a difference between the reconstruction signal and the acquired bio signal.

The bio signal pattern of the patient may be a pattern that is periodically repeated in the measured bio signal.

The method may further include dividing the acquired bio signal into a plurality of periods to obtain divided bio signals when there is no bio signal pattern of the patient; and averaging a predetermined number of the divided bio signals having a predetermined degree of similarity to each other to generate the bio signal pattern of the patient; and the generating of the reconstruction signal may include generating the reconstruction signal using the bio signal pattern of the patient.

The method may further include selecting the predetermined number of the divided bio signals having the predetermined similarity to each other based on correlation values between the divided bio signals.

The generating of the reconstruction signal may include generating the reconstruction signal by successively connecting bio signal patterns of the patient with each other so that locations of peaks in the bio signal patterns of the patient correspond to locations of peaks in the acquired bio signal.

The generating of the reconstruction signal may further include estimating the locations of the peaks in the acquired bio signal; and the successively connecting of the bio signal patterns of the patient with each other may include successively connecting the bio signal patterns of the patient so that the locations of the peaks in the bio signal patterns of the patient coincide with the estimated locations of the peaks in the acquired bio signal.

The eliminating of the motion artifacts may include performing adaptive filtering using the reconstruction signal as a target signal and the acquired bio signal as an input signal.

The performing of the adaptive filtering may include performing the adaptive filtering using a least means square (LMS) filter.

The acquired bio signal may be an electrocardiogram (ECG) signal.

A non-transitory computer-readable storage medium may store a computer program for controlling a computer to perform the method described above.

In another general aspect, an apparatus for eliminating motion artifacts in a bio signal includes a bio signal acquisition unit configured to acquire a bio signal from a patient; a reconstruction signal generator configured to generate a reconstruction signal of the acquired bio signal based on a result of comparing the acquired bio signal with a bio signal pattern of the patient generated using a bio signal measured from the patient before acquiring the bio signal from the patient; and a motion artifact elimination unit configured to eliminate motion artifacts in the acquired bio signal based on a difference between the reconstruction signal and the acquired bio signal.

The apparatus may further include a bio signal pattern generator configured to divide the acquired bio signal into a plurality of periods to obtain divided bio signals when there is no bio signal pattern of the patient; and average a predetermined number of the divided bio signals having a predetermined degree of similarity to each other to generate the bio signal pattern of the patient; and the reconstruction signal generator may be further configured to generate the reconstruction signal using the bio signal pattern of the patient.

The bio signal pattern generator may be further configured to select the predetermined number of the divided bio signals having the predetermined degree similarity to each other based on correlation values between the divided bio signals.

The reconstruction signal generator may be further configured to generate the reconstruction signal by successively connecting bio signal patterns of the patient with each other so that locations of peaks in the bio signal patterns of the patient correspond to locations of peaks in the acquired bio signal.

The reconstruction signal generator may include a peak estimation unit configured to estimate the locations of the peaks in the acquired bio signal; and a pattern matching unit configured to generate a reconstruction signal by successively connecting the bio signal patterns of the patient with each other so that the locations of the peaks in the bio signal patterns of the patient coincide with the estimated locations of the peaks in the acquired bio signal.

The motion artifact elimination unit may be further configured to perform adaptive filtering using the reconstruction signal as a target signal and the acquired bio signal as an input signal.

The motion artifact elimination unit may be further configured to perform the adaptive filtering using a least means square (LMS) filter.

Other features and aspects will be apparent from the following detailed description, the drawings, and the claims.

DETAILED DESCRIPTION

Figure 1:
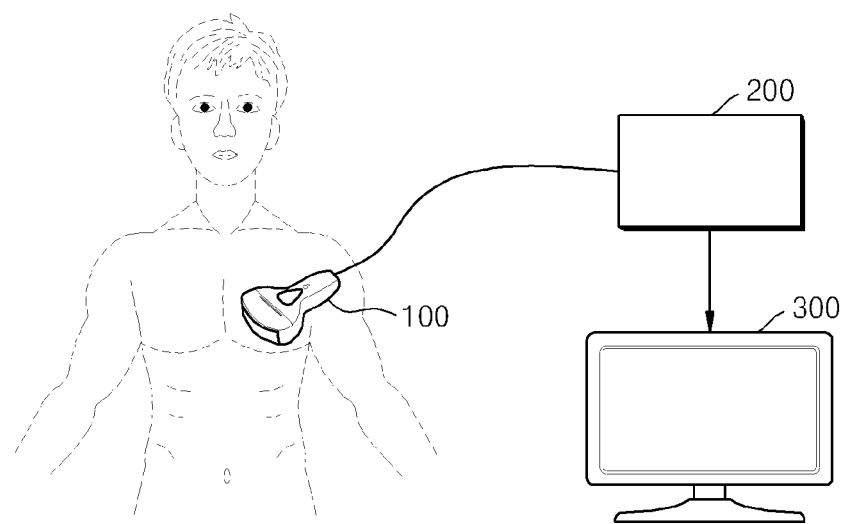
FIG. 1 is a block diagram of an example of a motion artifact elimination system.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a block diagram of an example of a motion artifact elimination system. Referring to FIG. 1, the motion artifact elimination system includes a detection probe 100, a motion artifact eliminating apparatus 200, and a display apparatus 300.

The detection probe 100 is an apparatus for detecting changes in a patient's body to determine a status of the patient. For example, the detection probe 100 may be an electrode disposed on the patient's body to obtain an electrocardiogram (ECG). The detection probe 100 outputs detected bio signals to the motion artifact eliminating apparatus 200.

The motion artifact eliminating apparatus 200 removes motion artifacts existing in bio signals detected by the detection probe 100. Bio signals are signals detecting changes in a human body, and may be, for example, an ECG, a ballistocardiogram (BCG), or a photoplethysmograph (PPG). Such bio signals of the patient need to be measured in his/her everyday life, and noise occurring due to movement of the patient has to be removed while measuring the bio signals of the patient in his/her everyday life. Noise generated in the bio signal due to the movement of the patient in his/her everyday life is referred to as a motion artifact. The motion artifact eliminating apparatus 200 eliminates motion artifacts and outputs bio signals free of the motion artifacts to the display apparatus 300.

The display apparatus 300 displays the bio signals whose motion artifacts are eliminated by the motion artifact eliminating apparatus 200. The signals displayed by the display apparatus 300 may be analyzed by a medical specialist or by the patient.

Figure 2:
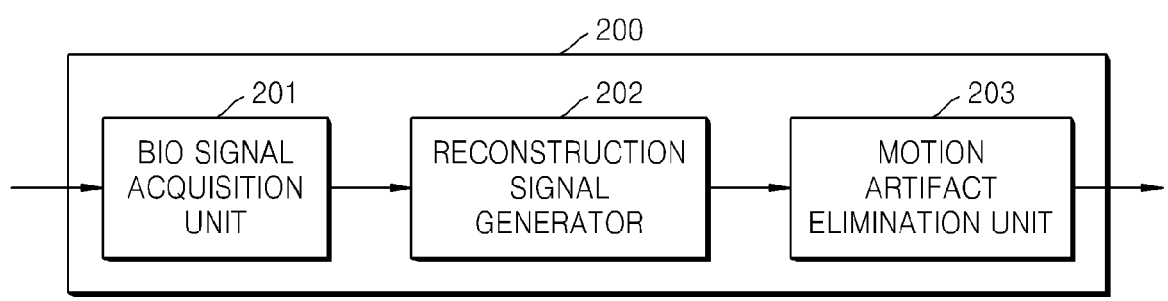
FIG. 2 is a block diagram of an example of a motion artifact eliminating apparatus of FIG. 1.

FIG. 2 is a block diagram of an example of the motion artifact eliminating apparatus 200 of FIG. 1. Referring to FIG. 2, the motion artifact eliminating apparatus 200 includes a bio signal acquisition unit 201, a reconstruction signal generator 202, and a motion artifact elimination unit 203.

The bio signal acquisition unit 201 acquires a bio signal from the patient. In this example, the bio signal acquired by the bio signal acquisition unit 201 is an ECG of the heart, and the bio signal acquisition unit 201 acquires the ECG of the heart and outputs the ECG to the reconstruction signal generator 202.

The reconstruction signal generator 202 compares the acquired bio signal with a bio signal pattern of the patient generated using a bio signal measured in advance from the patient, and generates a reconstruction signal of the acquired bio signal according to a result of the comparing. The bio signal pattern is extracted from the bio signal measured from the patient in advance, and represents a periodic pattern of the measured bio signal.

The bio signal of the heart generally has a periodic waveform, and has a pattern in which different signals are periodically repeated. The bio signal pattern is a pattern in which the different signals are periodically repeated, and the pattern varies for each person, similar to how finger prints vary for each person. Therefore, when the reconstruction signal generator 202 uses the bio signal pattern of the patient to be examined, rather than bio signal patterns of other people, the motion artifact elimination may be performed more accurately.

The reconstruction signal generator 202 generates a reconstruction signal under an assumption that there is no motion artifact in the bio signal. The reconstruction signal generator 202 generates the reconstruction signal by successively connecting bio signal patterns of the patient to each other. In this example, the bio signal patterns are the patient's own bio signal patterns, but this is merely an example, and other bio signal patterns may be used, such as standard bio signal pattern, an ideal bio signal pattern, a composite bio signal pattern obtained by combining bio signals of a plurality of patients, or any other suitable bio signal pattern. When the reconstruction signal generator 202 generates the reconstruction signal, the bio signal patterns of the patient are successively connected to each other, and locations of peaks in the acquired bio signal and locations of peaks in the bio signal pattern coincide with each other. Although the acquired bio signal is a periodic signal, a heartbeat rate may vary depending on an environment of the patient or a health condition of the patient, thereby changing the period of the acquired bio signal and the matching between the locations of the peaks in the acquired bio signal and the locations of the peaks in the bio signal pattern. Therefore, the reconstruction signal generator 202 extracts locations of peaks in a signal whose motion artifacts have been eliminated by the motion artifact elimination unit 203, and generates the reconstruction signal using the extracted locations. The above operations are repeatedly performed by the reconstruction signal generator 202. The processes of extracting the locations of the peaks and generating the reconstruction signal using the extracted locations of the peaks performed by the reconstruction signal generator 202 will be described in greater detail with reference to the block diagram of the example of the reconstruction signal generator 202 shown in FIG. 3.

The motion artifact elimination unit 203 eliminates motion artifacts of the acquired bio signal based on a difference between the reconstruction signal generated by the reconstruction signal generator 202 and the acquired bio signal. The reconstruction signal generated by the reconstruction signal generator 202 is generated under an assumption that there is no motion artifact in the bio signal, and the locations of peaks in the reconstruction signal coincide with the locations of peaks in the acquired bio signal. Therefore, the difference between the acquired bio signal and the reconstruction signal is calculated, and then the acquired bio signal is changed to minimize the difference to remove the motion artifacts.

Figure 3:
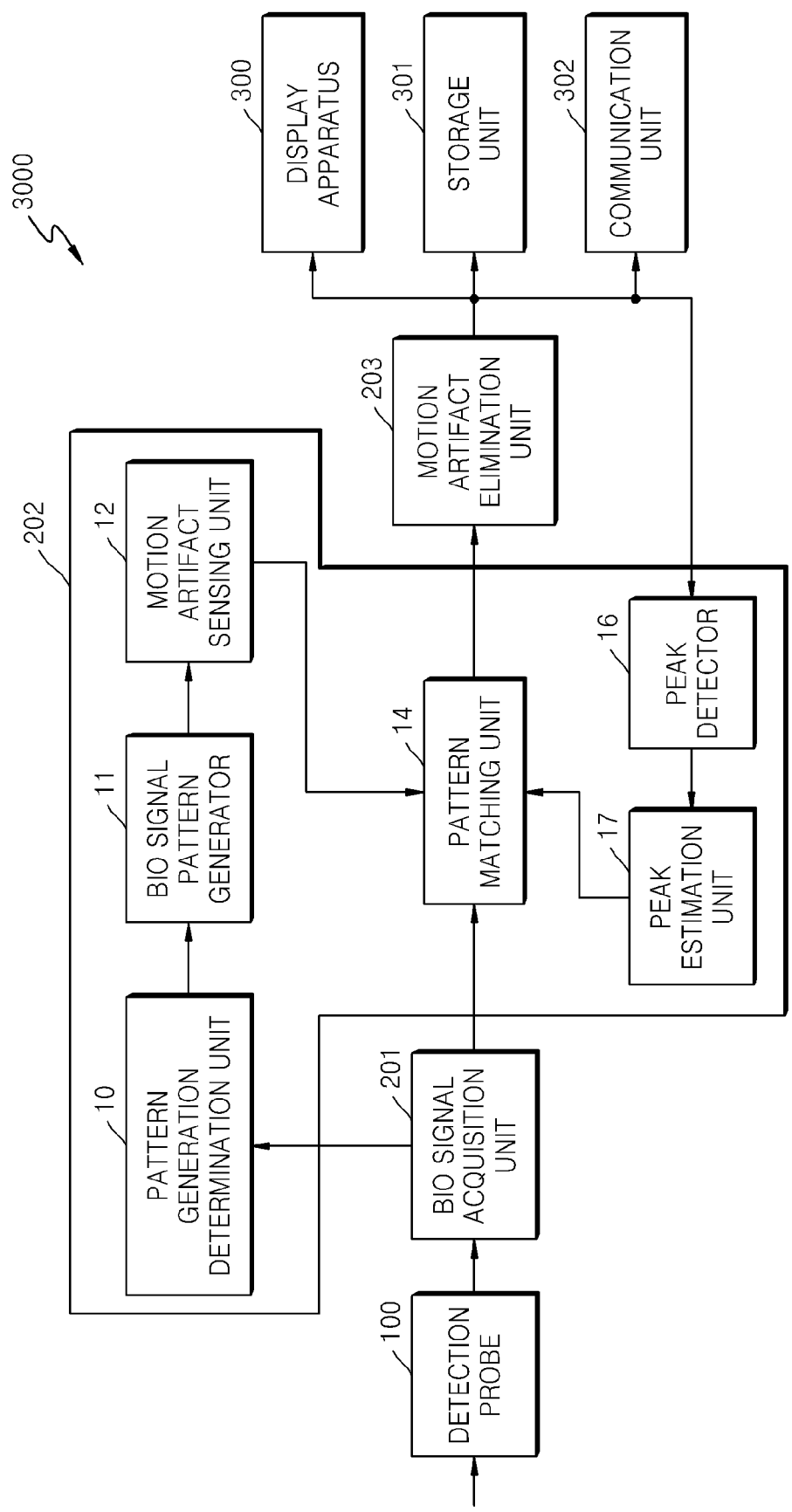
FIG. 3 is a detailed block diagram of an example of a bio signal detection system.

FIG. 3 is a detailed block diagram of an example of a bio signal detection system 3000. Referring to FIG. 3, the bio signal detection system 3000 includes the detection probe 100, the bio signal acquisition unit 201, the reconstruction signal generator 202, the motion artifact elimination unit 203, the display apparatus 300, a storage unit 301, and a communication unit 302. The bio signal acquisition unit 201, the reconstruction signal generator 202, and the motion artifact elimination unit 203 constitute the motion artifact eliminating apparatus 200 in FIGS. 1 and 2. The reconstruction signal generator 202 includes a pattern generation determination unit 10, a bio signal pattern generator 11, a motion artifact sensing unit 12, a pattern matching unit 14, a peak detector 16, and a peak estimation unit 17. The detection probe 100 and the display apparatus 300 are the same as those explained with reference to FIGS. 1 and 2, and thus detailed descriptions thereof will not be repeated here.

The pattern generation determination unit 10 determines whether a bio signal pattern of a patient is stored in the storage unit 301 when a bio signal of the patient is input via a connection that is not shown in FIG. 3. For example, the pattern generation determination unit 10 determines whether the bio signal pattern of the patient is stored in the storage unit 301 when the bio signal acquisition unit 201 starts acquiring a bio signal of a different patient.

An example of determining whether the bio signal pattern of the patient is stored in the storage unit 301 by the pattern generation determination unit 10 is as follows. When generating the bio signal pattern, the bio signal pattern generator 11 assigns an identification number of the patient to the bio signal pattern and stores the bio signal pattern with the identification number of the patient in the storage unit 301. The pattern generation determination unit 10 receives the identification number of the patient with the bio signal of the patient's heart, and determines whether there is the bio signal pattern corresponding to the identification number stored in the storage unit 301 to determine whether the bio signal pattern of the patient is stored in the storage unit 301. The bio signal pattern generator 11 may generate the identification number based on name, age of the patient, and disease name, or any other information about the patient.

Another example of determining of whether the bio signal pattern of the patient is stored in the storage unit 301 by the pattern generation determination unit 10 is as follows. The pattern generation determination unit 10 calculates a correlation value between the input bio signal of the heart and a stored bio signal pattern. When the calculated correlation value is equal to or greater than a predetermined value, the pattern generation determination unit 10 determines that the stored bio signal pattern and the bio signal of the heart belong to the same patient. For example, the pattern generation determination unit 10 may determine that the input bio signal of the heart and the stored bio signal pattern belong to the same patient when the calculated correlation value is 0.85 or greater.

If a plurality of bio signal patterns are stored in the storage unit 301, the pattern generation determination unit 10 calculates a correlation value between each of the stored bio signal patterns and the input bio signal of the heart. The pattern generation determination unit 10 determines that a stored bio signal pattern having a correlation value that is equal to or greater than the predetermined value is the bio signal pattern of the patient whose bio signal is being input. If there are a plurality of stored bio signal patterns having correlation values that are equal to or greater than the predetermined value, the pattern generation determination unit 10 determines that the bio signal pattern having the largest correlation value is the bio signal pattern of the patient whose bio signal is being input.

The pattern generation determination unit 10 provides an address of the stored bio signal pattern in storage unit 301 determined to be the bio signal pattern of the patient to the motion artifact sensing unit 12 and the pattern matching unit 14 via connections that are not shown in FIG. 1. If the pattern generation determination unit 10 determines that the bio signal pattern of the patient is not stored in the storage unit 301, the pattern generation determination unit 10 requests the bio signal pattern generator 11 to generate a bio signal pattern of the patient.

When the bio signal pattern generator 11 receives a request for generating a bio signal pattern of the patient from the pattern generation determination unit 10, the bio signal pattern generator 11 generates the bio signal pattern of the patient.

Figure 4:
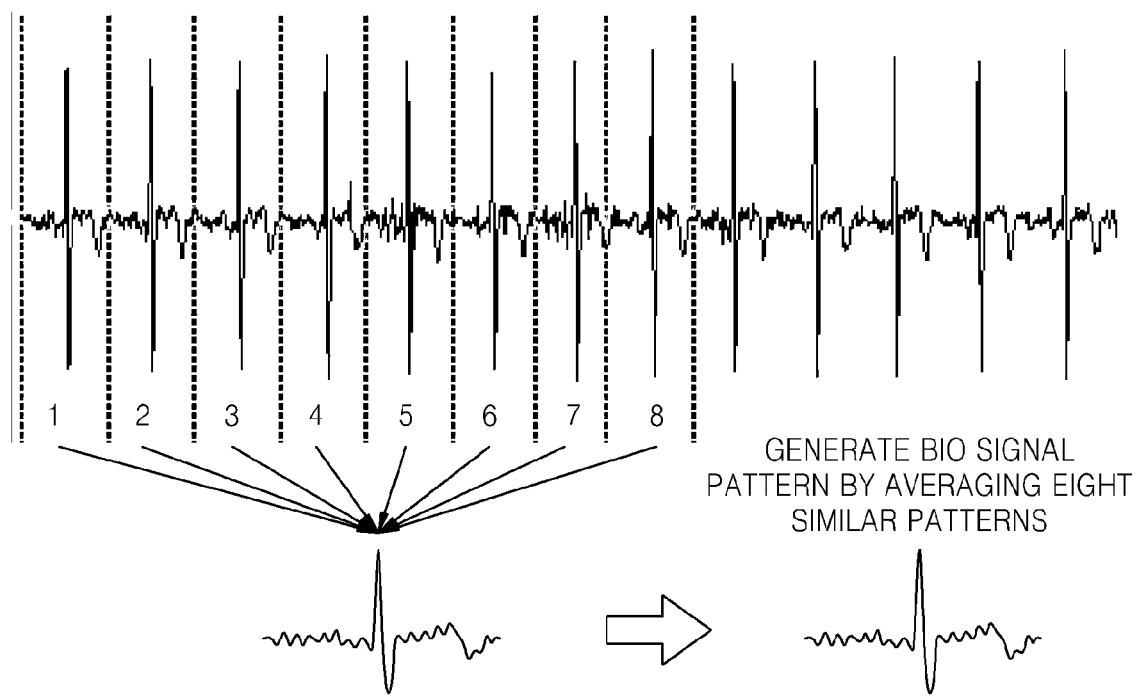
FIG. 4 is a diagram illustrating an example of a method of generating an electrocardiogram (ECG) and a bio signal pattern of a patient performed by a bio signal pattern generator of FIG. 3.

FIG. 4 is a diagram illustrating an example of a method of generating an ECG and a bio signal pattern of the patient performed by the bio signal pattern generator 11. When there is no bio signal pattern of the patient stored in the storage unit 301, the bio signal pattern generator 11 divides the acquired bio signal in period units, and averages a predetermined number of periodic bio signals having a high degree of similarity among the divided periodic bio signals to generate the bio signal pattern of the patient. The signal shown in an upper portion of FIG. 4 is an example of the ECG. In this example, the bio signal of the heart is an ECG, but the bio signal may be any bio signal. In the ECG shown in FIG. 4, similar patterns are repeated in similar time intervals. Time intervals of the repeated pattern are denoted by the dotted lines in FIG. 4. Although the time intervals are not exactly the same as each other, they are similar to each other, and the similar patterns are repeated in the similar time intervals. In this example, the bio signal pattern generator 11 detects R peaks of the input ECG to partition the similar patterns that are repeated in the similar time intervals. An R peak occurs when the ventricles contract, and is the highest point in the ECG. In addition, after detecting the R peaks of the input ECG, the bio signal pattern generator 11 may distinguish one pattern from other similar patterns based on the detected R peaks.

For example, the bio signal pattern generator 11 may set a 10th peak to the left of an R peak and a 15th peak to the right of the R peak as boundaries of one pattern. The bio signal pattern generator 11 analyzes the signal in a stable state, that is, when there is no motion artifact in the ECG, when generating the bio signal pattern. That is, when there is no bio signal pattern for a user stored in the storage unit 301, the bio signal pattern generator 11 transmits a signal indicating that there is no bio signal pattern stored in the storage unit 301 to the user. When the user recognizes from the signal that there is no bio signal pattern for the user stored in the storage unit 301, the user minimizes his/her movement to avoid generating any motion artifacts before generating the bio signal pattern to provide an environment necessary for the bio signal pattern generator 11 to accurately generate the bio signal pattern.

In FIG. 4, 8 patterns that are repeated are numbered, and an average pattern of the 8 patterns is calculated as shown in a lower left portion of FIG. 4. The average pattern is referred to as a bio signal pattern. However, the number of patterns used to calculate the average pattern is not limited to eight, and any suitable number of patterns may be used. However, among the patterns that are distinguished, there may be a pattern that is significantly different from the average pattern of the other patterns. For example, while the bio signal pattern generator 11 generates the bio signal pattern, motion artifacts may be generated due to movement of the user, and thus there may be one pattern that is significantly different from the other 7 patterns. This pattern may cause the bio signal pattern to differ from the actual average pattern, and so the bio signal pattern generator 11 may exclude the pattern that is significantly different from the other 7 patterns when calculating the average pattern.

The process of identifying a pattern that is significantly different from the other patterns when the bio signal pattern generator 11 generates the bio signal pattern will now be described in greater detail. The bio signal pattern generator 11 calculates the correlation values between the patterns, and excludes any pattern having a correlation value that is less than a predetermined value when calculating the average pattern of the patterns. When the correlation value is less than the predetermined value, this indicates that the pattern is significantly different from the other patterns, i.e., that the pattern has a low degree of similarity to the other patterns. When there are excluded patterns, the bio signal pattern generator 11 may extract a number of other patterns of the ECG equal to the number of excluded patterns so that the same number of patterns are always used by the bio signal pattern generator 11 in calculating the average pattern.

In the example described above, the bio signal generator 11 generates the bio signal pattern using 8 patterns. In this example, if one pattern has a correlation value of less than 0.85 compared to the other 7 patterns, the bio signal pattern generator 11 excludes the one pattern when generating the bio signal pattern. In addition, the bio signal pattern generator 11 may extract an additional pattern from the ECG to replace the excluded pattern, and generate the average bio signal pattern using a total of 8 patterns including 7 patterns that were originally extracted and the additional pattern that is extracted as shown in a lower right portion of FIG. 4. The additional pattern that is extracted is not shown in FIG. 4. The bio signal pattern generator 11 stores the bio signal pattern in the storage unit 301, and outputs the bio signal pattern to the motion artifact sensing unit 12.

When the ECG signal of the patient is input, the motion artifact sensing unit 12 determines whether the ECG signal includes motion artifacts. After determining whether motion artifacts are included in the ECG signal, the motion artifact sensing unit 12 outputs the ECG signal to an output apparatus or an apparatus for analyzing the ECG signal if there is no motion artifact in the ECG signal via connections that are not shown in FIG. 3. If the motion artifact sensing unit 12 determines that motion artifacts are included in the ECG signal, the motion artifact sensing unit 12 outputs the ECG signal to the pattern matching unit 14 of the reconstruction signal generator 202 to eliminate the motion artifacts.

A example of a process of determining whether motion artifacts exist in the input ECG signal performed by the motion artifact sensing unit 12 is as follows. When the ECG signal is input to the motion artifact sensing unit 12, the motion artifact sensing unit 12 calculates the correlation value between the ECG signal and the bio signal pattern. The bio signal pattern may be generated by the bio signal pattern generator 11 and output to the motion artifact sensing unit 12, or may be stored at the address of the storage unit 301 output by the pattern generation determination unit 10 to the motion artifact sensing unit 12.

When the motion artifact sensing unit 12 calculates the correlation value, locations of the R peaks of the ECG signal and the R peaks of the bio signal pattern are detected, and the correlation value is calculated based on the detected R peaks of the ECG signal and the detected R peaks of the bio signal pattern. The motion artifact sensing unit 12 calculates the correlation value of the ECG signal and the bio signal pattern, and determines that there are motion artifacts in the ECG signal when the calculated correlation value is less than a predetermined value. For example, the motion artifact sensing unit 12 may determine that there are motion artifacts in the ECG signal when the calculated correlation value is less than 0.9.

If the motion artifact sensing unit 12 determines that there are no motion artifacts in the ECG signal, the motion artifact sensing unit 12 directly outputs the ECG signal to the output apparatus or to the apparatus for analyzing the ECG signal.

If the motion artifact sensing unit 12 determines that there are motion artifacts in the ECG signal, the motion artifact sensing unit 12 outputs the ECG signal to the pattern matching unit 14 to eliminate the motion artifacts.

The pattern matching unit 14 outputs a signal obtained by matching the bio signal pattern to the current period of the input ECG signal. The current period is a period of the ECG signal that is currently being input. The pattern matching unit 14 matches the bio signal pattern to the current period of the input ECG signal based on locations of R peaks received from the peak estimation unit 17 The peak estimation unit 17 estimates the locations of the R peaks. For example, when the pattern matching unit 14 receives the estimated location of the R peak in an nth period of the ECG signal from the peak estimation unit 17, the pattern matching unit 14 matches the bio signal pattern to the ECG signal of the nth period.

Figure 5A:
FIGS. 5A and 5B are diagrams illustrating an example of a pattern matching process performed by a pattern matching unit of FIG. 3.
Figure 5B:
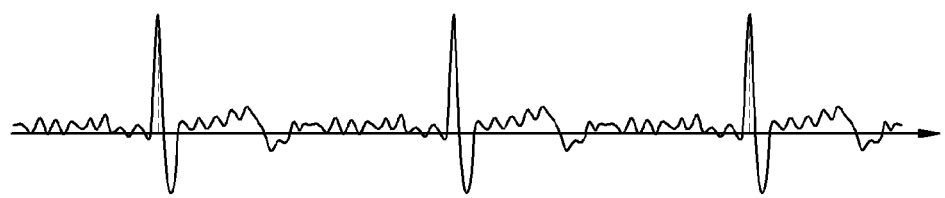

FIGS. 5A and 5B are diagrams showing an example of a pattern matching process performed by the pattern matching unit 14. FIG. 5A is a diagram showing locations of the R peaks estimated by the peak estimation unit 17. The peak estimation unit 17 estimates the locations of the R peaks of the ECG signal and outputs the estimated locations of the R peaks to the pattern matching unit 14. When the pattern matching unit 14 receives the estimated locations of the R peaks of the ECG signal as shown in FIG. 5A, the pattern matching unit 14 matches the bio signal pattern to the estimated locations of the R peaks. FIG. 5B is a diagram showing a result of the pattern matching unit 14 matching the bio signal pattern to the estimated locations of the R peaks of the ECG signal. When the pattern matching unit 14 matches the bio signal pattern to the estimated locations of the R peaks of the ECG signal, the estimated locations of the R peaks of the ECG signal and locations of the R peaks of the bio signal pattern coincide with each other. In addition, since the period of the ECG signal may vary to some degree, if the bio signal pattern is only matched to the estimated locations of the R peaks of the ECG signal, the left and right ratios of the bio signal pattern may not be matched with each other. For example, if the heartbeat of the user is fast due to strenuous exercise, the period between the R peaks of the ECG signal will be reduced. When the period is reduced, an interval between the R peaks is decreased. Thus, when the pattern matching unit 14 matches the bio signal pattern to the estimated locations of the R peaks of the ECG signals, the matched bio signal pattern of the previous period and the matched bio signal pattern of the current period may overlap with each other. When the two matched bio signal patterns overlap with each other, the pattern matching unit 14 adjusts the left and right ratios of the matched bio signal pattern of the current period so that the point where the matched bio signal pattern of the previous period ends and the point where the matched bio signal pattern of the current period begins coincide with each other.

The pattern matching unit 14 performs the pattern matching process described above when the heartbeat rate (beats per minute) of the patient becomes slower. When the patient relaxes or sleeps, the heartbeat rate may decrease. In this case, there will be a gap between the point where the matched bio signal pattern of the previous period ends and the point where the matched bio signal pattern of the current period begins. Therefore, the pattern matching unit 14 adjusts the left and right ratios of the bio signal pattern of the current period so that the point where the matched bio signal pattern of the previous period ends and the point where the bio signal pattern of the current period begins coincide with each other. The pattern matching unit 14 outputs the original ECG signal and the bio signal pattern matched to the original ECG signal to the motion artifact elimination unit 203. Although in this example, the pattern matching unit 14 matches the bio signal pattern to the original ECG signal when the heartbeat decreases, the pattern matching unit 14 may also match the bio signal pattern to the original ECG signal when the heartbeat increases.

The motion artifact elimination unit 203 eliminates the motion artifact in the ECG signal by performing an adaptive filtering operation. The adaptive filtering operation transforms an input signal so that the input signal is similar to a target signal. That is, the motion artifact elimination unit 203 performs the adaptive filtering operation using the bio signal pattern matched to the original ECG signal as the target signal. The motion artifact elimination unit 203 calculates an error between the original ECG signal and the bio signal pattern matched to the original ECG signal, and changes the original ECG signal to minimize the error. In this example, the motion artifact elimination unit 203 is implemented using a least means square (LMS) filter. However, any other adaptive filter known to one of ordinary skill in the art may be used to implement the motion artifact elimination unit 203.

Figure 6:
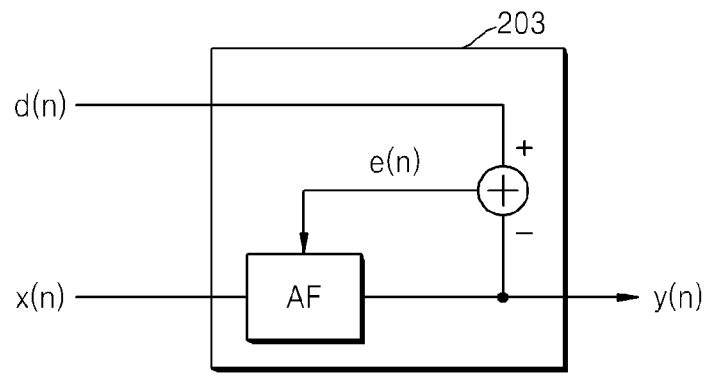
FIG. 6 is a diagram illustrating an example of a motion artifact elimination unit of FIG. 3 implemented as an LMS filter.

FIG. 6 is a diagram showing an example of the motion artifact elimination unit 203 of FIG. 3 implemented using an LMS filter. In the LMS filter of FIG. 6, inputs are x(n) and d(n) and an output is y(n). The LMS filter is a type of adaptive filter (AF), and calculates a least means square value of the signal errors and calculates a filter coefficient using the least means square value to imitate an ideal filter (or an ideal signal). When it is assumed that the inputs and the output of the LMS filter are discontinuous signals, the output of the LMS filter may be represented by the following Equation 1.

$$y(n) = \sum_{k=0}^{N-1} h(n)x(n-k) \tag{1}$$

In Equation 1, y(n) denotes an output, x(n) denotes an input, h(n) denotes a filter coefficient, n denotes an nth sampling bio signal pattern, with n ranging from 0 to M, M denotes the number of sampling bio signal patterns, N=2M−1, and k denotes an integer ranging from 0 to N−1. When it is assumed that the target signal of the motion artifact elimination unit 203 is d(n), an error between the target signal d(n) and the actual output signal y(n) may be represented by the following Equation 2.

$$e(n)=d(n)-y(n) \tag{2}$$

In Equation 2, e(n) denotes the error. A sum of squares of the error e(n) may be represented by the following Equation 3.

$$\epsilon = \sum_{n=0}^{M} e^2(n) \tag{3}$$

In equation 3, $\epsilon$ denotes a sum of squares of the error e(n). The motion artifact elimination unit 203 determines a value of h(n) for minimizing the sum of squares of the error e(n), and in general, the value of h(n) is determined using stochastic gradient descent (SGD) algorithm. In determining the value of h(n) that minimizes the sum of squares of the error, it may be difficult or impossible to calculate the value using a mathematical equation. According to the SGD algorithm, a gradient of an error function is calculated, and the value of h(n) that is a filter parameter is moved to an inclination having the sharpest gradient and the value of $\epsilon$ is calculated. The above processes are repeatedly performed to find a convergence value of h(n). The process of finding the convergence value of h(n) is represented by the following Equation 4.

$$h(k+1)=h(k)+2\mu e(k)x(k-n) \tag{4}$$

In Equation 4, $\mu$ denotes a step size for performing the repetition, and the process is stable within a range of $$0 < \mu < \frac{1}{10NP_x}.$$

$P_x$ may be defined by the following Equation 5.

$$P_x = \frac{1}{M}\sum_{n=0}^{M} x^2(n) \tag{5}$$

The LMS filter obtains the value of h(n) that is the filter coefficient, and finally outputs y(n) that is obtained by applying the value of h(n) to Equation 1. Basic principles of the LMS filter and the SGD algorithm are well known to one of ordinary skill in the art, and thus will not be described here.

The motion artifact elimination unit 203 calculates the error between the original ECG signal and the bio signal pattern matched to the original ECG signal using the LMS filter, and changes the original ECG signal to minimize the error. Since the bio signal pattern matched to the original ECG signal is a signal obtained under an assumption that there is no motion artifact, the bio signal pattern matched to the original ECG signal is an ideal signal. On the other hand, motion artifacts may occur in the original ECG signal due to the movement of the patient, and thus the motion artifact elimination unit 203 modifies the original ECG signal in which the motion artifacts are included to be similar to the bio signal pattern matched to the original ECG signal. In other words, the motion artifact elimination unit 203 imitates the ideal signal in which no motion artifact exists represented by the bio signal pattern matched to the original ECG signal through the adaptive filtering, and outputs the modified original ECG signal in which the motion artifact has been eliminated. The modified original ECG signal in which the motion artifact has been eliminated output from the motion artifact elimination unit 203 may be output to the apparatus for analyzing the ECG signal or the output apparatus for displaying the ECG. In addition, the modified original ECG signal in which the motion artifact has been eliminated output from the motion artifact elimination unit 203 is output to the peak detector 16 to be used in estimating locations of R peaks of the original ECG signal in a next period.

The peak detector 16 detects locations of the R peaks of the modified original ECG signal in which the motion artifact has been eliminated in the current period to estimate locations of the R peaks of the original ECG signal in the next period. A process of detecting the locations the R peaks of the modified original ECG signal in the current period performed by the peak detector 16 is as follows. The peak detector 16 detects locations of R peaks in the modified original ECG signal in which the motion artifact has been eliminated in the current period. A location of an R peak may be defined as a location where a signal intensity is equal to or greater than a predetermined value. For example, when the peak detector 16 detects a location where the signal intensity of the modified original ECG signal in which the motion artifact has been eliminated is 1 or greater, the peak detector 16 determines that an R peak exists at that location, and determines that location as the location of the R peak. However, the signal intensity of 1 is merely an example, and the peak detector 16 may use any desired signal intensity to determine whether an R peak exists. The peak detector 16 then detects a location of an R peak in the original ECG signal in the current period based on the detected location of the R peak in the modified original ECG signal in which the motion artifact has been eliminated in the current period. In greater detail, the peak detector 16 detects the signal having the highest intensity within a range of −10 milliseconds (ms) to +10 ms in the original ECG signal from the detected location of the R peak in the modified original ECG signal in which the motion artifact has been eliminated as the R peak of the original ECG signal. Since the original ECG signal includes the motion artifact, it is not easy to detect the R peak in the original ECG signal. However, when a range for detecting the R peak is limited to a narrow range around the location of the R peak in the modified ECG signal from which the motion artifact has been eliminated, an accuracy of the detection of the R peak in the original ECG signal may be improved. Although the peak detector 16 uses a range of −10 ms to +10 ms in this example, this is merely an example, and other ranges may be used. The peak detector 16 outputs the detected location of the R peak in the original ECG signal in the current period to the peak estimation unit 17.

When the bio signal is not an ECG signal, but another bio signal such as a ballistocardiogram (BCG) signal or a photoplethysmograph (PPG) signal, locations of signal features corresponding to the R peaks of the ECG signals may be detected. For example, the peak detector 16 may detect a signal feature at an instant when ventricles of the heart contract in the BCG signal or the PPG signal.

The peak estimation unit 17 estimates a location of the R peak in the original ECG signal in the next period based on the location of the R peak in the original ECG signal in the current period detected by the peak detector 16. For example, when the peak detector 16 detects the location of the R peak in the original ECG signal in an nth period representing the current period, the peak estimation unit 17 estimates a location of the R peak in the original ECG signal in an (n+1)st period. A process of estimating the location of the R peak in the original ECG signal in the (n+1)st period is as follows. The peak estimation unit 17 estimates a location in the original ECG signal obtained by adding the period of the original ECG signal to the location of the R peak in the original ECG signal in the nth period as the location of the R peak in the original ECG signal in the (n+1)st period. Since the period of the ECG signal is not constant, the peak estimation unit 17 may use an average of the (n−10)th to (n−1)st periods of the ECG signal as the period of the ECG signal. For example, if it is assumed that the location of the R peak in the original ECG signal in the nth period is 6.54 seconds and the period of the original ECG signal is 1.20 seconds, the peak estimation unit 17 estimates the location of the R peak in the original ECG signal in the (n+1)st period as 6.54 seconds+1.20 seconds=7.74 seconds.

The display apparatus 300 displays the bio signal measured by the motion artifact eliminating apparatus 200. For example, the display apparatus 300 may be a display panel, a liquid crystal display (LCD) screen, or a monitor provided in the bio signal detection system 3000.

One of ordinary skill in the art will appreciate that the bio signal detection system 3000 may not include the display apparatus 300, and may include the communication unit 302 for outputting the bio signal measured by the motion artifact eliminating apparatus 200 to an external display apparatus (not shown in FIG. 3).

The storage unit 301 stores data generated during operation of the bio signal detection system 3000. The storage unit 301 may be a hard disk drive (HDD), a random access memory (RAM), a flash memory, a memory card, or any other memory device known to one of ordinary skill in the art capable of storing data generated during operation of the system bio signal detection system 3000.

The communication unit 302 transmits data to and receives data from an external apparatus through a wired or wireless network, a wired serial connection, or any other type of connection known to one of ordinary skill in the art. The external apparatus may be another medical imaging system located at a remote location, a universal computing system, a personal digital assistant (PDA), a portable terminal, a facsimile apparatus, or any other device known to one of ordinary skill in the art capable of receiving the bio signal output by the bio signal detection system 3000.

Examples of the network include the Internet, a local area network (LAN), a wireless LAN (WLAN), a wide area network (WAN), a personal area network (PAN), and any other type of network capable of transmitting data known to one of ordinary skill in the art.

In addition, the storage unit 301 and the communication unit 302 may be integrated into a picture archiving and communication system (PACS) that provides image reading and searching functions.

Accordingly, the bio signal detection system 3000 may display, store, or output the bio signal measured by the motion artifact eliminating apparatus 200 to an external apparatus. Thus, utilization of the bio signal measured by the motion artifact eliminating apparatus 200 may be improved.

Figure 7:
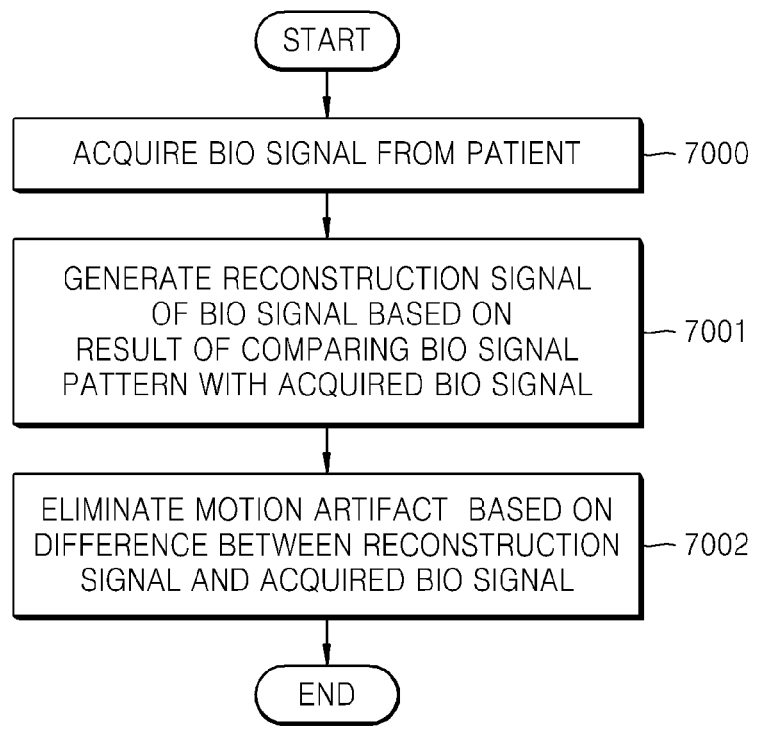
FIG. 7 is a flowchart illustrating an example of a method of eliminating motion artifacts.

FIG. 7 is a flowchart illustrating an example of a method of eliminating motion artifacts. In operation 7000, the bio signal acquisition unit 201 acquires a bio signal from a patient. The bio signal is the same as the bio signal described above with reference to the bio signal acquisition unit 201, and thus a detailed description thereof will not be repeated here. In operation 7001, the reconstruction signal generator 202 generates the reconstruction signal of the acquired bio signal according to a result of comparing the bio signal pattern with the acquired bio signal. The bio signal pattern and the reconstruction signal have been described above, and thus detailed descriptions thereof will not be repeated here. In operation 7002, the motion artifact elimination unit 203 eliminates a motion artifact in the acquired bio signal based on a difference between the reconstruction signal and the acquired bio signal.

Figure 8:
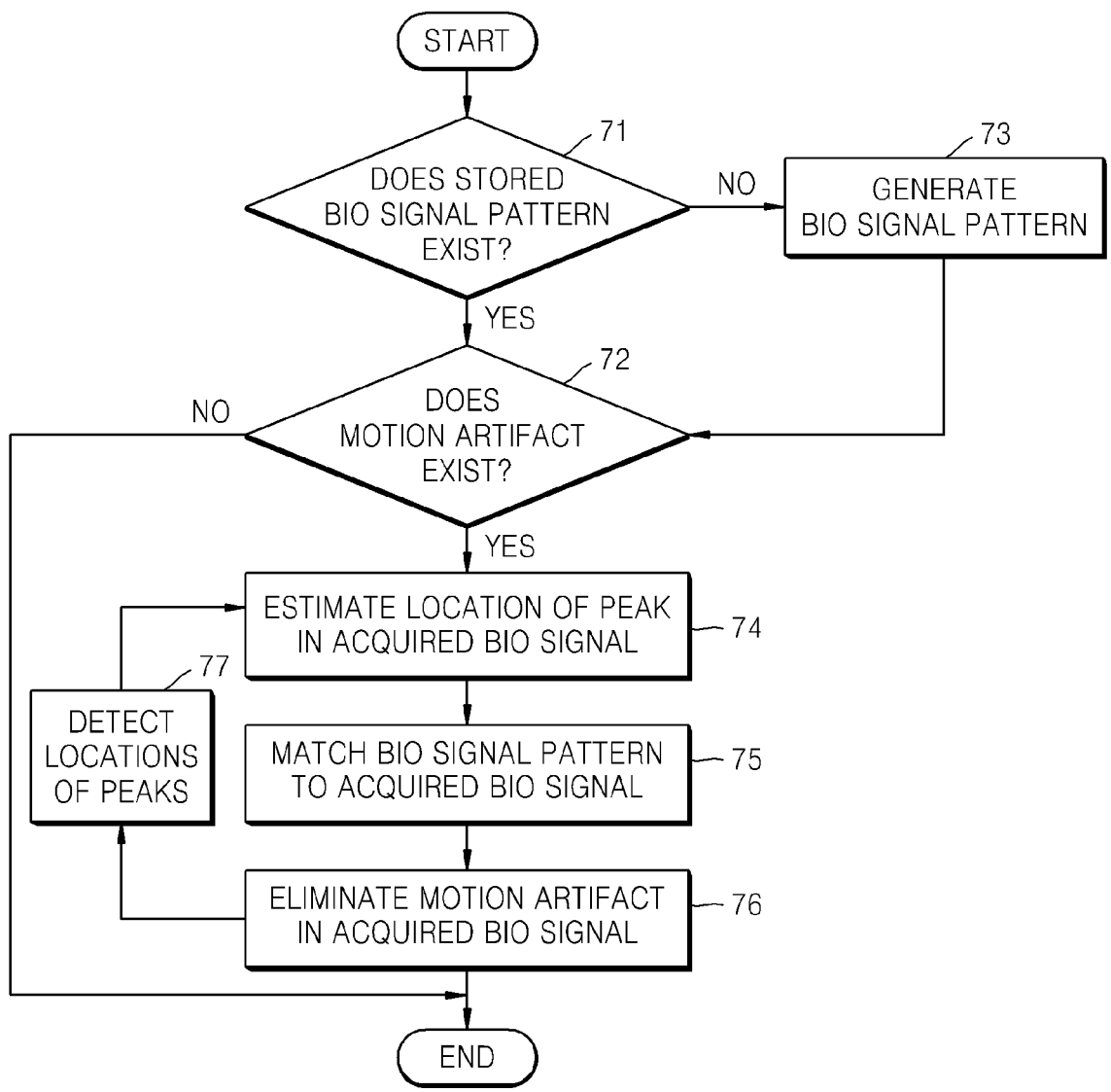
FIG. 8 is a flowchart illustrating an example of another method of eliminating motion artifacts.

FIG. 8 is a flowchart illustrating an example of another method of eliminating motion artifacts. In operation 71, the pattern generation determination unit 10 determines whether there is a stored bio signal pattern when a bio signal is acquired from a patient. When the pattern generation determination unit 10 determines that there is no stored bio signal pattern in operation 71, the pattern generation determination unit 10 requests the bio signal pattern generator 11 to generate the bio signal pattern in operation 73, and then the process goes to operation 72. When the pattern generation determination unit 10 determines that there is a stored bio signal pattern in operation 71, the process goes directly to operation 72. In operation 72, the motion artifact sensing unit 12 determines whether there is a motion artifact in the acquired bio signal. If the motion artifact sensing unit 12 determines that there is no motion artifact in operation 72, the process ends. If the motion artifact sensing unit 12 determines that there is a motion artifact in operation 72, the process goes to operation 74. In operation 74, the peak estimation unit 17 estimates a location of a peak in the acquired bio signal in a current period based on a location of a peak in the acquired bio signal in a previous period. In operation 75, the pattern matching unit 14 matches the bio signal pattern to the estimated location of the peak in the acquired bio signal in the current period estimated by the peak estimation unit 17. In operation 76, the motion artifact elimination unit 203 eliminates the motion artifact in the acquired bio signal by performing an adaptive filtering operation. In operation 77, the peak detector 16 detects a location of a peak in the modified acquired bio signal from which the motion artifact has been eliminated by the motion artifact elimination unit 203 in a current period, detects a location of a peak in the acquired bio signal in the current period based on the detected location of the peak in the modified acquired bio signal from which the motion artifact has been eliminated in the current period, and outputs the detected location of the peak in the acquired bio signal in the current period to the peak estimation unit 17 for use as the location of the peak in the acquired bio signal in the previous period in operation 74.

As described above, the various examples enable motion artifacts in a bio signal, such as bio signal of a heart, that occur in the everyday life of a patient to be eliminated effectively, and thus the bio signal may be measured reliably and continuously during the everyday life of the patient.

The motion artifact eliminating apparatus 200, the bio signal acquisition unit 201, the reconstruction signal generator 202, the motion artifact elimination unit 203, the pattern generation determination unit 10, the bio signal pattern generator 11, the motion artifact sensing unit 12, the pattern matching unit 14, the peak detector 16, the peak estimation unit 17, the communication unit 302, and the LMS filter described above may be implemented using one or more hardware components, one or more software components, or a combination of one or more hardware components and one or more software components.

A hardware component may be, for example, a physical device that physically performs one or more operations, but is not limited thereto. Examples of hardware components include amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features and aspects in each example are to be considered as being applicable to other similar features and aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of eliminating motion artifacts in a bio signal, the method comprising:
    acquiring a bio signal from a patient;
    generating a reconstruction signal of the acquired bio signal by successively connecting bio signal patterns of the patient with each other so that locations of peaks in the bio signal patterns of the patient correspond to locations of peaks in the acquired bio signal; and
    eliminating motion artifacts in the acquired bio signal based on a difference between the reconstruction signal and the acquired bio signal.

2. The method of claim 1, wherein the bio signal patterns of the patient are a pattern that is periodically repeated in a bio signal measured from the patient.

3. The method of claim 1, further comprising:
    dividing the acquired bio signal into a plurality of periods to obtain divided bio signals; and
    averaging a predetermined number of the divided bio signals having a predetermined degree of similarity to each other to generate a bio signal pattern of the patient;
    wherein the successively connecting of the bio signal patterns of the patient with each other comprises successively connecting a plurality of the generated bio signal pattern of the patient with each other so that locations of peaks in the plurality of the generated bio signal pattern of the patient correspond to the locations of peaks in the acquired bio signal.

4. The method of claim 3, further comprising selecting the predetermined number of the divided bio signals having the predetermined similarity to each other based on correlation values between the divided bio signals.

5. The method of claim 1, wherein the generating of the reconstruction signal further comprises estimating the locations of the peaks in the acquired bio signal; and
    the successively connecting of the bio signal patterns of the patient with each other comprises successively connecting the bio signal patterns of the patient so that the locations of the peaks in the bio signal patterns of the patient coincide with the estimated locations of the peaks in the acquired bio signal.

6. The method of claim 1, wherein the eliminating of the motion artifacts comprises performing adaptive filtering using the reconstruction signal as a target signal and the acquired bio signal as an input signal.

7. The method of claim 6, wherein the performing of the adaptive filtering comprises performing the adaptive filtering using a least means square (LMS) filter.

8. The method of claim 1, wherein the acquired bio signal is an electrocardiogram (ECG) signal.

9. A non-transitory computer-readable storage medium storing a computer program for controlling a computer to perform the method of claim 1.

10. The method of claim 1, wherein the successively connecting of the bio signal patterns of the patient with each other comprises adjusting respective widths of the bio signal patterns so that each bio signal pattern ends where a next bio pattern signal begins in the bio signal patterns successively connected with each other.

11. An apparatus for eliminating motion artifacts in a bio signal, the apparatus comprising:
    a bio signal acquisition unit configured to acquire a bio signal from a patient;
    a reconstruction signal generator configured to generate a reconstruction signal of the acquired bio signal by successively connecting bio signal patterns of the patient with each other so that locations of peaks in the bio signal patterns of the patient correspond to locations of peaks in the acquired bio signal; and
    a motion artifact elimination unit configured to eliminate motion artifacts in the acquired bio signal based on a difference between the reconstruction signal and the acquired bio signal.

12. The apparatus of claim 11, wherein the bio signal patterns of the patient are a pattern that is periodically repeated in a bio signal measured from the patient.

13. The apparatus of claim 11, further comprising a bio signal pattern generator configured to:

divide the acquired bio signal into a plurality of periods to obtain divided bio signals; and average a predetermined number of the divided bio signals having a predetermined degree of similarity to each other to generate a bio signal pattern of the patient;

wherein the reconstruction signal generator is further configured to successively connect the bio signal patterns of the patient with each other by successively connecting a plurality of the generated bio signal pattern of the patient with each other so that locations of peaks in the plurality of the generated bio signal pattern of the patient correspond to the locations of peaks in the acquired bio signal.

14. The apparatus of claim 13, wherein the bio signal pattern generator is further configured to select the predetermined number of the divided bio signals having the predetermined degree similarity to each other based on correlation values between the divided bio signals.

15. The apparatus of claim 11, wherein the reconstruction signal generator comprises:

a peak estimation unit configured to estimate the locations of the peaks in the acquired bio signal; and a pattern matching unit configured to generate the reconstruction signal by successively connecting the bio signal patterns of the patient with each other so that the locations of the peaks in the bio signal patterns of the patient coincide with the estimated locations of the peaks in the acquired bio signal.

16. The apparatus of claim 11, wherein the motion artifact elimination unit is further configured to perform adaptive filtering using the reconstruction signal as a target signal and the acquired bio signal as an input signal.

17. The apparatus of claim 16, wherein the motion artifact elimination unit is further configured to perform the adaptive filtering using a least means square (LMS) filter.

18. The apparatus of claim 11, wherein the acquired bio signal is an electrocardiogram (ECG) signal.

19. The apparatus of claim 11, wherein the reconstruction signal generator is further configured to adjust respective widths of the bio signal patterns so that each bio signal pattern ends where a next bio pattern signal begins in the bio signal patterns successively connected with each other.

* * * * *